United States Patent [19]

Buckle et al.

[11] 4,223,032
[45] Sep. 16, 1980

[54] TRIAZOLO [4,5-B] QUINOLINES AND PROPHYLAXIS OF ALLERGIC DISEASES WITH THEM

[75] Inventors: Derek R. Buckle, Redhill; Harry Smith, Maplehurst, Nr. Horsham, both of England

[73] Assignee: Beecham Group Limited, England

[21] Appl. No.: 955,599

[22] Filed: Oct. 30, 1978

[30] Foreign Application Priority Data

Nov. 10, 1977 [GB] United Kingdom ............... 46764/77

[51] Int. Cl.$^2$ .................. A61K 31/475; C07D 471/14; C07D 471/22
[52] U.S. Cl. ...................................... 424/258; 546/64; 546/82
[58] Field of Search ...................... 546/64, 82; 424/258

[56] References Cited

U.S. PATENT DOCUMENTS 3,992,539  11/1976  Eloy et al. ........................... 424/258

OTHER PUBLICATIONS

Tiagi, et al., Chemical Abstracts, vol. 77, 139775q (1972).

Schaefer, et al. Chemical Abstracts, vol. 84, 164,739h (1976).

Primary Examiner—Donald G. Daus
Assistant Examiner—Diana G. Rivers
Attorney, Agent, or Firm—Jacobs & Jacobs

[57] ABSTRACT

The invention provides novel compounds of formula (I).

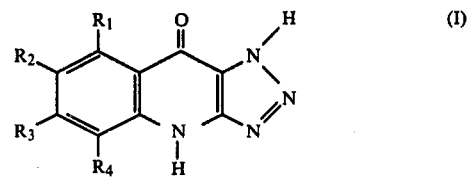

and pharmaceutically acceptable salts thereof wherein $R_1$, $R_2$, $R_3$ and $R_4$ which may be the same or different, represent hydrogen, halogen, lower alkyl, and lower alkoxy, or any adjacent two of $R_1$ to $R_4$ taken together represent an alkylene group containing from 3 to 5 carbon atoms or a 1,4-buta-1,3-dienylene group. The compounds are useful as anti-allergic agents.

6 Claims, No Drawings

TRIAZOLO [4,5-B] QUINOLINES AND PROPHYLAXIS OF ALLERGIC DISEASES WITH THEM

This invention relates to a novel class of 4,9-dihydro-9-oxo-1H-triazolo[4,5-b] quinolines, to their use as anti-allergic agents, to pharmaceutical compositions comprising such compounds and to a method for their preparation.

It is generally recognised that certain cells e.g. mast cells are activated by antibody-antigen combinations and release substances such as histamine and SRS-A which mediate an allergic response. We have discovered a novel class of 4,9-dihydro-9-oxo-1H-triazolo[4,5-b] quinoline derivatives which inhibit this type of antigen-induced response in mammals, and are therefore of value in the prophylaxis of diseases in which the symptoms are controlled by mediators of the allergic response. Examples of such diseases include bronchial asthma, rhinitis, hayfever and allergic eczema.

Accordingly, the present invention provides a compound of formula (I):

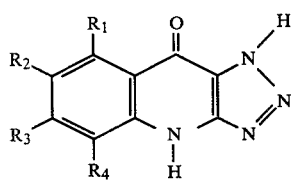

and pharmaceutically acceptable salts thereof wherein $R_1$, $R_2$, $R_3$ and $R_4$ which may be the same or different, represent hydrogen, halogen, lower alkyl, and lower alkoxy, or any adjacent two of $R_1$ to $R_4$ taken together represent an alkylene group containing from 3 to 5 carbon atoms or a 1,4-buta-1,3-dienylene group.

By lower alkyl and lower alkoxy, we mean such groups containing up to six carbon atoms.

Examples of suitable lower alkyl groups which $R_1$ to $R_4$ represent, include methyl, ethyl and n-propyl.

Examples of suitable lower alkoxy groups which $R_1$ to $R_4$ represent include methoxy, ethoxy and n-propoxy.

Examples of suitable halogens which $R_1$ to $R_4$ represent include fluorine and chlorine.

Where compounds (I) are highly substituted, it is appreciated that the substituents $R_1$ to $R_4$ are selected for steric compatability.

The triazole moiety of the compounds of formula (I) has an acidic hydrogen, and accordingly may form salts. Examples of pharmaceutically acceptable salts falling within the scope of this invention include the aluminium salt, alkali metal and alkaline earth metal salts such as the sodium, potassium and magnesium salt; and salts with organic bases such as amines or amino compounds.

Within the group of compounds of general formula (I) there is one preferred sub-group of compounds in which $R_1$ and $R_4$ are hydrogen and $R_2$ and $R_3$ which may be the same or different, represent hydrogen, methyl, ethyl or n-propyl.

Examples of such compounds are:
4,9-Dihydro-9-oxo-1H-triazolo[4,5-b] quinoline,
4,9-dihydro-7-methyl-9-oxo-1H-triazolo[4,5-b] quinoline and
4,9-dihydro-6,7-dimethyl-9-oxo-1H-triazolo[4,5-b] quinoline.

Compounds of formula (I) can be prepared by an intra-molecular cyclization of a corresponding 4-arylamino-1,2,3-triazole-5-carboxylic acid derivative (II) below.

Accordingly, the invention further provides a method for preparing a compound of formula (I) or a pharmaceutically acceptable salt thereof which method comprises the intra-molecular cyclization of a compound of formula (II):

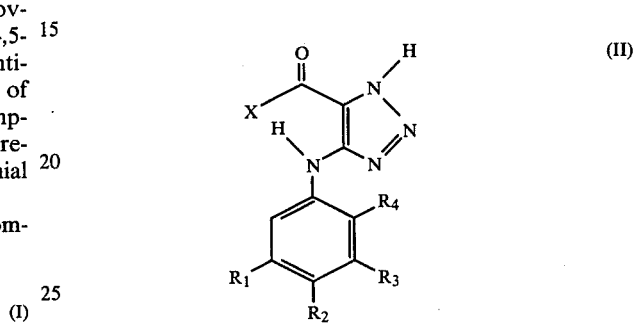

wherein $R_1$ to $R_4$ are as defined with reference to formula (I) above, and X is hydroxyl or an active substituent such that —COX is an acylating derivative, in the presence of a cyclising agent, and thereafter where desired, salifying the product so obtained.

When X is hydroxyl, the cyclisation is preferably carried out using polyphosphoric acid.

Examples of activating substituents include halides (i.e. X is halogen) particularly the chloride and bromide. Where X is a halogen the cyclising agent is suitably a Friedel Crafts catalyst, examples of which include aluminium chloride and stannic chloride.

The reaction may be carried out in the absence of a solvent, particularly when the cyclising agent is polyphosphoric acid. However, if desired, the reaction may be carried out in a solvent which is inert to the reagents and products.

This method is best carried out at elevated temperatures i.e. above 60° but less than 120° C., particularly when the cyclizing agent is polyphosphoric acid. We have found 100° C. to be convenient.

The carboxylic acids (II) where X is OH i.e. (IIa), are prepared as shown in the following scheme:

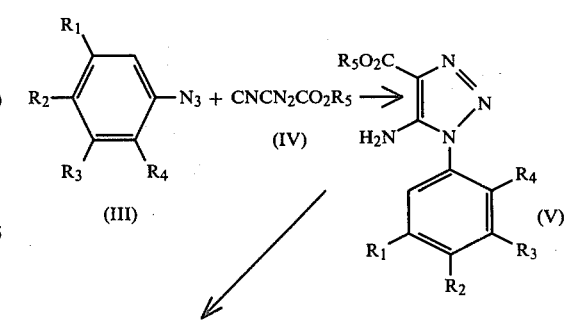

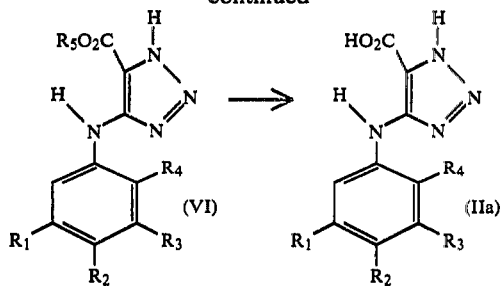

in which $R_1$ to $R_4$ are as previously defined in the text, and $R_5$ is an organic group such that $-CO_2R_5$ is an ester. (The carboxylic acids (IIa) may be converted to an acylating derivative (II) by standard methods.)

In the above scheme, a cyano acetic acid ester (IV) is condensed with an appropriate azide (III) in the presence of a strong base such as sodium ethoxide. This reaction, which may be carried out by the method of O. Dimroth. Annalen 364, 183 (1909), gives the triazole (V). Triazoles of formula (V) undergo the Dimroth rearrangement (O. Dimroth loc. cit.) on heating with a base such as sodium ethoxide or pyridine to produce a 4-arylamino-triazole-ester (VI). A number of 4-arylaminotriazoles (VI) have been reported in the literature. Aqueous alkaline hydrolysis of the 4-arylaminotriazole ester (VI) liberates the free carboxylic acid, (IIa).

In order to use compounds of formula (I) or salts thereof for medical purposes, they are formulated in accordance with standard pharmaceutical practice as pharmaceutical compositions.

The invention further provides pharmaceutical compositions comprising a compound of formula (I) above or a pharmaceutically acceptable salt thereof together with a pharmaceutically acceptable carrier.

Compounds of formula (I) may be administered topically or systemically. In accordance with usual pharmaceutical procedure, the active material will be purified so as to contain minimum amounts of by-products or other impurities.

Topical formulations for administration to the skin include lotions and creams. Topical formulations for administration to the respiratory tract include solutions for application via a nebulizer, aerosols, snuffs and microfine insufflatable powders. The active ingredient in an insufflatable powder has a small particle size i.e. less than 50 microns and preferably less than 10 microns. The active material is co-presented with a solid carrier such as lactose which has a particle size of less than 50 microns. Insufflatable compositions in particular will be rendered substantially free of microbial contaminants.

Systemic administration may be achieved by rectal, oral or parenteral administration. A typical suppository formulation comprises the active compound with a binding and/or lubricating agent such as gelatin or cocoa butter or other low melting vegetable waxes or fats. Typical parenteral compositions comprise a solution or suspension of the active material in a sterile aqueous carrier or parenterally acceptable oil.

Compounds of formula (I) which are active when given orally may be compounded in the form of syrups, tablets, capsules and lozenges. A syrup formulation will generally consist of a suspension or solution of the compound in a suitable liquid carrier such as ethyl alcohol, glycerine or water with a flavouring or colouring agent.

Where the composition is in the form of a capsule, the solid in granular form optionally with a binding agent is encapsulated in an edible shell e.g. of gelatin. Where the composition is in the form of a tablet, any suitable pharmaceutical carrier routinely used for preparing solid formulations may be used. Examples of such carriers include magnesium stearate, starch, lactose, glucose, sucrose, rice flour and chalk. Preferably the composition is in unit dose form such as a pill, capsule or metered aerosol so that the patient may administer to himself a single dose.

Where appropriate, small amounts of anti-asthmatics and bronchodilators for example sympathomimetic amines such as isoprenaline, isoetharine, salbutamol, phenylephrine and ephedrine; xanthine derivatives such as theophylline and aminophylline; and corticosteroids such as prednisolone and adrenal stimulants such as ACTH may be included. As is common practice, the compositions will usually be accompanied by written or printed directions for use in the medical treatment concerned, in this case as an anti-allergic agent for treatment of, for example, asthma, hay-fever or rhinitis.

The following examples illustrate the invention.

EXAMPLE 1

(a) Ethyl 5-amino-1-phenyl-1,2,3-triazole-4-carboxylate

A solution of sodium (2.04 g; 0.089 mole) in ethanol (50 ml) was added to a mixture of phenyl azide (11.9 g; 0.1 mole) and ethyl cyanoacetate (11.3 g; 0.1 mole) and the product gently warmed to 45° C. with stirring for 5 mins. After stirring at ambient temperature for a further 15 minutes the flask was immersed in water at room temperature for 3 hrs. A white solid separated which was filtered off after dilution of the mixture with water and washed with water. Recrystallisation from ethanol gave 18.4 g. (79%) of material of mp 124.5–125.5° C. (lit mp 126°; B. R. Brown, D. L. Hammick and S. G. Heritage *J. Chem. Soc.* 3820 [1953]).

(b) Ethyl-4-anilino-1,2,3-triazole-5-carboxylate

Ethyl 5-amino-1-phenyl-1,2,3-triazole-4-carboxylate (3.13 g; 0.0135 mole) was stirred at reflux with a solution of sodium (0.31 g; 0.135 atom) in ethanol (20 ml) for 3 hrs. and the mixture evaporated to dryness. The residual solid was dissolved in warm water, acidified and the precipitate filtered off to give 2.622 g (84%) of the title compound of mp 126–127° C. Recrystallisation from 90% ethanol gave material of mp 131–132° C. (lit mp 129–130° C.; O. Dimroth *Annalen* 364 183 [1909])

(c) 4Anilino-1,2,3-triazole-5-carboxylic acid

Hydrolysis of ethyl 4-anilino-1,2,3-triazole-5-carboxylate (9.29 g; 0.04 mole) with 1.25 N sodium hydroxide (200 ml) at 90° C. for 18 hrs. gave the free acid in quantitative yield. Recrystallisation from water containing a minimum of ethanol gave material of mp 149.5–150.5° C. (dec) (lit. mp. 153° C., O. Dimroth *Annalen* 364 183 [1909]), (Found; C, 52.88; H, 4.14; N, 27.36; $C_9H_8N_4O_2$ requires; C, 52.94; H, 3.95; N, 27.44%).

(d) 4,9-Dihydro-9-oxo-1H-triazolo[4,5-b] quinoline

A mixture of 4-anilino-1,2,3-triazole-4-carboxylic acid (1 g) and 85% polyphosphoric acid (10 g) was stirred at 100° C. for 6 hrs. cooled and diluted with water. The precipitated solid was filtered off and recrystallised from ethanol/N,N-dimethylformamide to give 0.762 g (84%) of the triazoloquinoline of mp 311–312° C. (dec) νmax. (mull) 2700 (broad), 1640 (broad), 1595 cm$^{-1}$. δ (TFA) 7.77–8.38 (3 H,m); 8.85 (1 H, d, J 9 Hz) (Found; C, 57.65; H, 3.57; N, 30.19; C$_9$H$_6$N$_4$O requires; C, 58.05; H, 3.25; N, 30.09%).

EXAMPLE 2

(a) Ethyl 5-amino-1-(p-tolyl)-1,2,3-triazole-4-carboxylate

Reaction of p-tolyl azide (9.38 g; 0.0705 mole) with ethyl cyanoacetate (7.96 g: 0.0705 mole) as described in example 1a gave 12.76 g (74%) of the triazole of mp (EtOH) 152–153° C. (lit mp 147.5° C., B. R. Brown, D. L. Hammick and S. G. Heritage *J. Chem. Soc.* 3870 [1953]). (Found; C, 58.38; H 5.90; N, 22.89; C$_{12}$H$_{14}$N$_4$O$_2$ requires; C, 58.52; H, 5.73; N, 22.75%).

(b) Ethyl 4-(p-tolylamino)-1,2,3-triazole-5-carboxylate

A solution of 5-amino-1-(p-tolyl)-1,2,3-traizole-4-carboxylate (10 g) in dry pyridine (50 ml) was heated at reflux for 6 hrs. cooled, diluted with water and acidified with hydrochloric acid. The precipitated solid was filtered off and extracted with 1 N sodium hydroxide (200 ml) from which the product was isolated after acidification. Recrystallisation from 90% ethanol gave 4.82 g (48%) of solid of mp 129–130° C., (Found; C, 58.35; H, 5.77; N, 22.60; C$_{12}$H$_{14}$N$_4$O$_2$ requires; C, 58.52; H, 5.73; N, 22.75%).

(c) 4-(p-tolylamino)-1,2,3-triazole-5-carboxylic acid

Hydrolysis of ethyl 4-(p-tolylamino)-1,2,3-triazole-5-carboxylate (4.5 g) with aqueous sodium hydroxide as described in example 1c, afforded 3.85 g (96%) of acid of mp (acetone-water) 144° C., (Found; C, 55.32; H, 4.86; N, 25.64; C$_{10}$H$_{10}$N$_4$O$_2$ requires; C, 55.04; H, 4.62; N, 25.77%).

(d) 4,9-dihydro-7-methyl-9-oxo-1H-triazolo[4,5-b]quinoline

Cyclisation of 4-(p-tolylamino)-1,2,3-triazole-5-carboxylic acid (1 g) with 85% polyphosphoric acid (12 g) at 100° C. over 2 hrs. gave 0.66 g (72%) of the title compound of mp (EtOH-DMF-H$_2$O) 310° C.; ν$_{max}$(mull) 2720 (br.) 1655, 1600 cm$^{-1}$, Δ (DMSO) 2.42 (3H, s); 7.58 (2H, s); 8.10 (1H,s), 1 low fieled broad (exchangeable). (Found; C, 59.89; H, 4.37; N, 28.09; C$_{10}$H$_8$N$_4$O$_2$ requires; C, 59.99 H, 4.03; N, 27.99%).

EXAMPLE 3

(a) Ethyl 5-amino-1-(p-chlorophenyl)-1,2,3-triazole-4-carboxylate

Reaction of p-chlorophenyl azide (7.48 g; 0.0487 mole) with ethyl cyanoacetate (5.5 g; 0.0487 mole) as described in example 1a gave 10.057 g (81%) of the triazole of mp (ethanol) 162–164° C. (lit mp 165–167° C.; Ger Offen No. 2,009,134[1970]) (Found; C, 49.78; H, 4.31; N, 21.15; C$_{11}$H$_{11}$ClN$_4$O$_2$ requires; C, 49.54; H, 4.16; N, 21.01%).

(b) Ethyl 4-(p-chlorophenylamino)-1,2,3-triazole-5-carboxylate

A solution of ethyl 5-amino-1-(p-chlorophenyl)-1,2,3-triazole-4-carboxylate (10 g) in dry pyridine (50 ml) was refluxed for 6 hrs. and the cooled solution poured into dilute hydrochloric acid. The precipitated solid was filtered off and recrystallised from 90% ethanol to give 10 g (100%) of the rearrangement product of mp 161° C. (lit mp 162° C. Ger. Offen No. 2,009,134 [1970]). (Found; C, 49.46; H, 4.31; N, 20.85; C$_{11}$H$_{11}$ClN$_4$O$_2$ requires; C, 49.54; H, 4.16; N, 21.01%).

(c) 4-Chlorophenylamino)-1,2,3-triazole-5-carboxylic acid

Ethyl 4-(p-chlorophenylamino)-1,2,3-triazole-5-carboxylate (5 g) was hydrolysed as described in example 1c to give the acid in quantitative yield. Recrystallisation from acetone-water gave material of mp 157° C. (dec). (Found; C, 45.43; H, 3.15; N, 23.45; C$_9$H$_7$ClN$_4$O$_2$ requires; C, 45.30; H, 2.96; N, 23.48%).

(d) 7-Chloro-4,9-dihydro-9-oxo-1H-triazolo[4,5-b]quinoline

Cyclisation of 4-(p-chlorophenylamino,-1,2,3-triazole-5-carboxylic acid (1 g) with 85% polyphosphoric acid (12 g) at 100° C. for 5 hrs. gave the triazole, 0.66 g (71%) which on recrystallisation from ethanol / N,N-dimethylformamide/H$_2$O had mp 313°–314° C. (dec) (Found; C, 48.76; H, 2.57; N, 24.99; Cl, 16.09; C$_9$H$_5$ClN$_4$O requires; C, 48.99; H, 2.28; N, 25.40; Cl, 16.07%).

Passive Cutaneous Anaphylaxis (PCA)

Serum containing heat labile homocytotropic antibody was raised in rats to crystallized ovalbumin XOA by the method of Mota (I. Mota, Immunology, 7,681 [1964] using Bordettela pertussis vaccine as adjuvant.

Passive cutaneous anaphylaxis (PCA) was carried out by a method based on that of Ovary and Bier, (A. Ovary and O. G. Bier, Proc. Soc. Exp. Biol. Med. 81, 584, [1952]) as modified by Goose and Blair. (Immunology 16, 749 [1969]).

Male Wistar rats of 250–300 g. were given 0.1 ml. of each of six twofold serial dilutions of pooled antiserum in 0.9% saline injected intradermally into separate sites on their shaved backs. Later (72 hrs.) the animals were challenged by intravenous injection of 0.3 ml. of a 1% solution of ovalbumin in an isotonic solution of saline buffered with 0.05 M, pH 7.2, Sorenson Buffer (PBS), mixed with 0.2 ml. of a 5% solution of Pontamine Sky Blue (6BX C.I. 24410, Raymond A. Lamb, London) in isotonic saline. The rats were killed after 20 min and the diameter of the blue wheals at the antibody injection sites was measured on the outer surface of the skin. The starting dilution of the serum was adjusted so that there was no response, after challenge, at the injection site of the highest dilution and a maximum response at the lowest dilutions. Typically six twofold serial dilutions of the serum from ¼ to 1/128 were used.

Compounds were tested for their ability to reduce the diameter of the wheals at those intradermal sites which in control animals gave less than maximum response. Each dose of the compound was administered to six rats at a measured time prior to intravenous challenge with ovalbumin. Control groups of six rats were given the same volume (0.2 ml/100 g) of carrier fluid at the same time prior to the challenge.

The results were calculated as follows. % inhibition of PCA = 100 (1 − a/b) where a = the sum of the diameters of the wheals produced in the test animal at the sites of antibody dilutions as used in control groups and b = the mean sum of the diameters of the wheals produced in the control group of animals at those antibody sites where at least five out of six of the animals gave less than maximum response. A typical variation in the control group of animals was SEM± 6%.

| Example | Route | Carrier Fluid | Time* (mins) | Dose mg/kg | % Inhib PCA |
|---------|-------|---------------|--------------|------------|-------------|
| 1 | i.v. | PBS with | 0 | 2 | 14 |
|   |      | NaHCO₃ | 0 | 4 | 22 |
|   |      |        | 0 | 10 | 79 |
| 2 | i.v. | PBS with | 0 | 5 | 16 |
|   |      | NaHCO₃ | 0 | 10 | 65 |
| 3 | i.v. | PBS with | 0 | 5 | 36 |
|   |      | NaHCO₃ | 0 | 20 | 70 |

*Time between administration of compound and antigen challenge.

Acute toxicity: no toxic symptoms were observed with any of the compounds while carrying out the tests described above.

What we claim is:

1. A compound of formula (I):

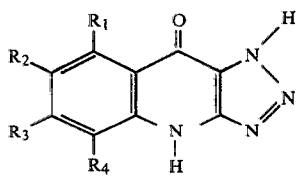

and pharamceutically acceptable salts thereof wherein $R_1$, $R_2$, $R_3$ and $R_4$ which may be the same or different, represent hydrogen, halogen, lower alkyl, lower alkoxy, or any adjacent two of $R_1$ to $R_4$ taken together represent an alkylene group containing from 3 to 5 carbon atoms or a 1,4-buta-1,3-dienylene group.

2. A compound according to claim 1 wherein $R_1$, $R_2$, $R_3$ and $R_4$ may represent hydrogen, methyl, ethyl, n-propyl, methoxy, ethoxy, n-propoxy, fluorine or chlorine.

3. A compound according to claim 1 wherein $R_1$ and $R_4$ are hydrogen and $R_2$ and $R_3$ represent hydrogen, methyl, ethyl or n-propyl.

4. A compound according to claim 1 selected from:
4,9-dihydro-9-oxo-1H-triazolo-[4,5-b]-quinoline,
4,9-dihydro-7-methyl-9-oxo-1H-triazolo[4,5-b]-quinoline,
4,9-dihydro-6,7-dimethyl-9-oxo-1H-triazolo[4,5-b]-quinoline and their pharmaceutically acceptable salts.

5. A pharmaceutical composition useful for the prophylaxis of allergic diseases comprising a compound according to claim 1 and a pharmaceutically acceptable carrier.

6. A method for the prophylaxis of allergic diseases which method comprises administering to a patient an effective amount of a compound according to claim 1.

* * * * *